(12) United States Patent
Corver et al.

(10) Patent No.: US 9,194,626 B2
(45) Date of Patent: Nov. 24, 2015

(54) MONITORING FREEZE DRYING WITH GAS MEASUREMENT ON VACUUM PUMP EXHAUST

(75) Inventors: Jozef A. W. M. Corver, Nuenen (NL); Carlo J. J. M. De Best, Raamsdonksveer (NL); Francis W. DeMarco, Niagra Falls, NY (US); David Debo, Batavia, NY (US)

(73) Assignee: IMA LIFE NORTH AMERICA INC., Tonawanta, NY (US)

( * ) Notice: Subject to any disclaimer, the term of this patent is extended or adjusted under 35 U.S.C. 154(b) by 688 days.

(21) Appl. No.: 13/516,315

(22) PCT Filed: Dec. 22, 2009

(86) PCT No.: PCT/US2009/006681
§ 371 (c)(1),
(2), (4) Date: Jun. 15, 2012

(87) PCT Pub. No.: WO2011/078835
PCT Pub. Date: Jun. 30, 2011

(65) Prior Publication Data
US 2012/0246964 A1    Oct. 4, 2012

(51) Int. Cl.
*F26B 5/06* (2006.01)
*G01M 3/20* (2006.01)
(Continued)

(52) U.S. Cl.
CPC .............. *F26B 5/06* (2013.01); *G01M 3/202* (2013.01); *G01M 3/22* (2013.01); *G01N 33/0014* (2013.01); *G01N 33/0016* (2013.01)

(58) Field of Classification Search
CPC ............. F26B 5/06; F26B 5/065; A23L 3/44; A61K 9/19; Y10S 159/05; A23B 7/024; A23B 4/037; A23B 5/03
USPC ..................................................... 34/284–301
See application file for complete search history.

(56) References Cited

U.S. PATENT DOCUMENTS

| | | | |
|---|---|---|---|
| 3,342,990 A | | 9/1967 | Barrington |
| 4,459,844 A | * | 7/1984 | Burkhart ........................ 73/40.7 |
| 4,488,118 A | | 12/1984 | Jeffers |

(Continued)

FOREIGN PATENT DOCUMENTS

| | | |
|---|---|---|
| EP | 0280540 A2 | 8/1988 |
| JP | 2005195327 | 7/2005 |

(Continued)

OTHER PUBLICATIONS

Japanese Office Action; Japanese Patent Office; Notification Reason for Rejection.

(Continued)

*Primary Examiner* — David J Laux

(57) ABSTRACT

Parameters of a freeze drying process are monitored by measuring trace materials in the vacuum pump exhaust. The measurements are made using techniques such as acousto-optic spectrometry, multipass cavity-enhanced absorption spectrometry (CEAS) and cavity ring-down spectrometry (CRDS). The technique may be used to diagnose problems such as leakage in the freeze drying shelves, leakage in the condensation coils, leaks from atmosphere in the chambers and the presence of residual cleaning materials. The technique may also be used to monitor the presence of water vapor in the exhaust of a secondary drying process.

30 Claims, 4 Drawing Sheets

(51) Int. Cl.
*G01M 3/22* (2006.01)
*G01N 33/00* (2006.01)

(56) References Cited

U.S. PATENT DOCUMENTS

| | | | |
|---|---|---|---|
| 4,622,845 A | | 11/1986 | Ryan |
| 4,865,871 A | * | 9/1989 | Livesey et al. ............... 435/1.3 |
| 4,918,975 A | | 4/1990 | Voss |
| 5,022,265 A | * | 6/1991 | Voss ............................... 73/40.7 |
| 5,115,666 A | * | 5/1992 | Williams ....................... 73/19.1 |
| 5,283,199 A | * | 2/1994 | Bacon et al. ................... 436/173 |
| 5,837,193 A | | 11/1998 | Childers |
| 6,227,036 B1 | | 5/2001 | Yonak |
| 6,327,896 B1 | * | 12/2001 | Veronesi et al. ........... 73/40.5 A |
| 6,848,196 B2 | | 2/2005 | Brulls |
| 6,875,399 B2 | * | 4/2005 | McVey ............................... 422/3 |
| 7,089,681 B2 | | 8/2006 | Herbert |
| 2001/0016278 A1 | | 8/2001 | Onishi et al. |
| 2005/0279646 A1 | * | 12/2005 | Hasegawa et al. ............ 205/789 |
| 2007/0157704 A1 | | 7/2007 | Jenneus et al. |
| 2010/0313634 A1 | | 12/2010 | Wetzig |

FOREIGN PATENT DOCUMENTS

| | | |
|---|---|---|
| JP | 2005195327 A | 7/2005 |
| WO | WO9411034 | 5/1994 |
| WO | WO2009091399 A1 | 7/2009 |

OTHER PUBLICATIONS

D-TEK Select; Refrigerant Leak Detector; INFICON; 2006.
Journal of Applied Physics; Ultralow Gas Concentration Infrared Absorption Spectroscopy; vol. 42, No. 7; Jun. 1971.
Reports; Nitric Oxide Air Pollution: Detection by Optoacoustic Spectroscopy; Jul. 2, 1971.
European Search Report, European Patent Office, Jul. 22, 2014.

* cited by examiner

MONITORING FREEZE DRYING WITH GAS MEASUREMENT ON VACUUM PUMP EXHAUST

FIELD OF THE INVENTION

The present invention relates generally to a freeze drying process for removing moisture from a product using vacuum and low temperature. More specifically, the invention relates to the problem of monitoring process parameters before, during and after the freeze drying operation is performed.

BACKGROUND

Freeze drying is a process that removes a solvent, typically water, from a product in the form of ice. While water is used in the present disclosure as the exemplary solvent, other solvents, such as alcohol, are also used in freeze drying processes and may be used with the presently disclosed methods and apparatus. In the freeze drying process, the product is frozen and, under vacuum, the ice sublimes and the vapor flows towards a condenser. The water or other solvent is condensed on the condenser as ice and is removed in a later stage. Freeze drying is particularly useful in the pharmaceutical industry, as the integrity of the product is preserved during the freeze drying process and product stability can be guaranteed over relatively long periods of time. The freeze dried product is ordinarily a biological substance and is commonly contained in vials.

As illustrated by the example freeze drying system 100 of FIG. 1, a batch of product 112 is placed on freeze dryer shelves 121 within a freeze drying chamber 110. The freeze dryer shelves 121 are hollow and are used to support the product and to transfer heat to and from the product as required by the process. A heat transfer fluid 114 flows through the shelves to remove or add heat.

Water vapor created by the sublimation of ice in the product 112 flows through a passageway 115 into a condensing chamber 120 containing condensing coils or other surfaces 122 maintained below the condensation temperature. A coolant 125 is passed through the coils 122 to remove heat, causing the water vapor to condense as ice on the coils.

Both the freeze drying chamber 110 and the condensing chamber 120 are maintained under vacuum during the process by a vacuum pump 150 having a low pressure inlet 151 connected to the exhaust of the condensing chamber 120. Non-condensable gases contained in the chambers 110, 120 are removed by the vacuum pump 150 and exhausted at a high pressure outlet 152.

Pharmaceutical freeze drying is an aseptic process that requires sterile conditions within the freeze drying chamber 110 and condenser chamber 120. A freeze drying cycle may last several days, and the quantity of product processed in a single batch may represent a very large investment. It is therefore critical to assure that the freeze drying system is sterile and leak-free before a cycle is commenced and for the duration of the cycle. Both the shelves in the freeze drying chamber and the coils in the condensing chamber are hollow, and contain heat transfer media. It is important to be able to detect any leakage of those non-sterile fluids into the process vessels should a leak occur.

In the condenser, the coolant media used may be of a very low viscosity, and have a low vapor pressure, making detection of a leak difficult. In the case of a condenser circuit that is cooled by direct expansion of a refrigerant, leakage of the gaseous refrigerant is also difficult to detect and is undesirable in the freeze drying process. In the freeze drying chamber, the hollow shelves are flushed by thermal fluid that is typically a silicone oil of very low viscosity. Those silicone oils also have a very low vapor pressure, making it very difficult to detect leakage. Therefore there is a need for leak detection, preferably real time, without disturbing the aseptic freeze drying process.

The chambers and connecting passages are under vacuum and are therefore required to maintain a high pressure differential across their walls. Any leakage of non-sterile ambient gases through the walls into the aseptic chambers must be detected as quickly and accurately as possible.

It has been proposed to perform a secondary drying operation wherein the condensing chamber 120 is temporarily bypassed by a passageway 130 in a final drying stage to remove small amounts of residual moisture. In the secondary drying operation, a small amount of residual water vapor from the product passes through the vacuum pump 150 and is contained in the vacuum pump exhaust. The secondary drying process is conceptually limited by the capacity of the vacuum pump to pump water vapor. One expected problem in performing a secondary drying operation is the adequate detection or measurement of moisture content in the product, for monitoring the progress of the operation. A system is needed for measuring water removal without interfering with the pharmaceutical drying process.

Most freeze dryer diagnostic techniques are direct, and analyze the condition of the gas in the drying chamber. Direct checking of leakage may be complicated with very large freeze dryers, where manual checking cannot be done. Further, if the leakage is related to certain time periods in the freeze-drying cycle, or related to certain high or low temperatures, the likelihood of detection might be minimal.

Examples of such in-situ low pressure analysis techniques are residual gas analysis using mass spectroscopy, and partial pressure gas analysis, for which there are many specialized methods. Several disadvantages are inherent in those technologies. The measurements of interest are taken at low pressure, meaning low concentrations that result in detection difficulties. Moreover, the gas streams within the freeze drying chamber and the condensation chamber contain a large amount of water (99%) from the drying process, which may overwhelm the measurement of other species.

The measurement technologies may interfere with the drying process. Those in-situ low-pressure detection technologies must, by nature, sample the gas flow within the sterile environment where freeze drying takes place. Many of those technologies, however, involve sensors that are not easily sterilized. Some of those technologies even create byproducts such as chemically reactive species that may affect the material that is being dried in unfavorable ways.

There is therefore a need for a technique for effectively monitoring a freeze drying process without disturbing the normal process routine. The technique should be easily automated, should not introduce contaminants into the process, and should detect, with high accuracy, leaks or other abnormalities in the process.

SUMMARY

The present disclosure addresses the needs described above by providing a method for analyzing a gas stream containing a solvent vapor. In the method, the solvent vapor is first removed from the gas stream to produce a non-condensable gas stream. The non-condensable gas stream is compressed to produce a compressed gas stream. A concentration of a material is then measured in the compressed gas stream.

The gas stream containing the solvent vapor may be an exhaust from a freeze drying chamber. The freeze drying chamber may include hollow freeze drying shelves containing a heat transfer fluid, in which case the material measured in the compressed gas stream is heat transfer fluid leaking from the shelves. The heat transfer fluid may contain a perfluorinated fluid, in which case a concentration of the perfluorinated fluid is measured using a halogen leak detector.

The step of removing the solvent vapor from the gas stream may include passing the gas stream through a condensation chamber containing cooled condensing surfaces. In that case, the measured material may be a medium for cooling the condensing surfaces that is leaking into the condensation chamber.

The measured material may be a residual cleaning material used in cleaning a process chamber. The cleaning material may be hydrogen peroxide ($H_2O_2$) or chlorine dioxide ($ClO_2$).

The measurement step may include using acousto-optic spectrometry to measure the concentration of the material. The measurement step may include using a measurement technique selected from the group consisting of multipass cavity-enhanced absorption spectrometry (CEAS) and cavity ring-down spectroscopy (CRDS).

Another embodiment of the method is a method for freeze drying a product. In that method, heat is removed from the product to freeze a solvent contained in the product. The frozen solvent in the product is sublimed to form a solvent vapor contained in a low-pressure gaseous effluent flowing away from the product. At least some of the solvent vapor is condensed from the low-pressure gaseous effluent, and the gaseous effluent is compressed using a vacuum pump. A concentration of at least one trace material is measured in the gaseous effluent on a high-pressure side of the vacuum pump.

The heat may be removed from the product using hollow freeze drying shelves containing a heat transfer fluid. The material measured in the gaseous effluent may be heat transfer fluid leaking from the shelves. The heat transfer fluid may contain a perfluorinated fluid, in which case the concentration of the perfluorinated fluid is measured using a halogen leak detector.

The condensation of solvent vapor from the low-pressure gaseous effluent may comprise passing the low-pressure gaseous effluent through a condensation chamber containing cooled condensing surfaces. In that case, the material measured in the gaseous effluent may be a medium for cooling the condensing surfaces.

The material measured in the gaseous effluent may be a residual cleaning material used in cleaning a process chamber. The cleaning material may be hydrogen peroxide (H2O2) or chlorine dioxide (ClO2).

Another embodiment of the invention is a freeze dryer system. The system includes a freeze drying chamber for containing product during the freeze drying process; a condensation chamber in communication with the freeze drying chamber and comprising surfaces for condensing solvent vapor from exhaust gas received from the freezer drying chamber; a vacuum pump having a low pressure inlet and a high pressure outlet, the low pressure inlet of the vacuum pump being in communication with the condensation chamber; and a testing apparatus connected for receiving exhaust gas from the high pressure outlet of the vacuum pump, the testing apparatus being for measuring a presence of a material contained in the exhaust gas.

The freeze drying chamber may include hollow freeze drying shelves containing a heat transfer fluid. In that case, the testing apparatus may measure trace amounts of heat transfer fluid from the shelves. The heat transfer fluid may contain a perfluorinated fluid, in which case the testing apparatus may be a halogen leak detector.

The surfaces for condensing solvent vapor in the condensation chamber may comprise cooled condensing surfaces. In that case, the testing apparatus may measure trace amounts of a medium for cooling the condensing surfaces that is leaking into the condensation chamber.

The testing apparatus may measure trace amounts of a residual cleaning material used to clean the process chamber. The cleaning material may be hydrogen peroxide (H2O2) or chlorine dioxide (ClO2).

The testing apparatus may be an acousto-optic spectrometer. The testing apparatus may be a multipass cavity-enhanced absorption spectrometer (CEAS) or cavity ring-down spectrometer (CRDS).

Yet another embodiment of the invention is a method for freeze drying a product. Heat is removed from the product in a freeze drying chamber to freeze a solvent contained in the product. The frozen solvent in the product is sublimed to form a solvent vapor contained in a low-pressure gaseous effluent flowing away from the product. The gaseous effluent is compressed using a vacuum pump. The process is monitored by measuring a concentration of solvent vapor in the gaseous effluent on the high-pressure side of the vacuum pump.

DESCRIPTION

Figure 1:
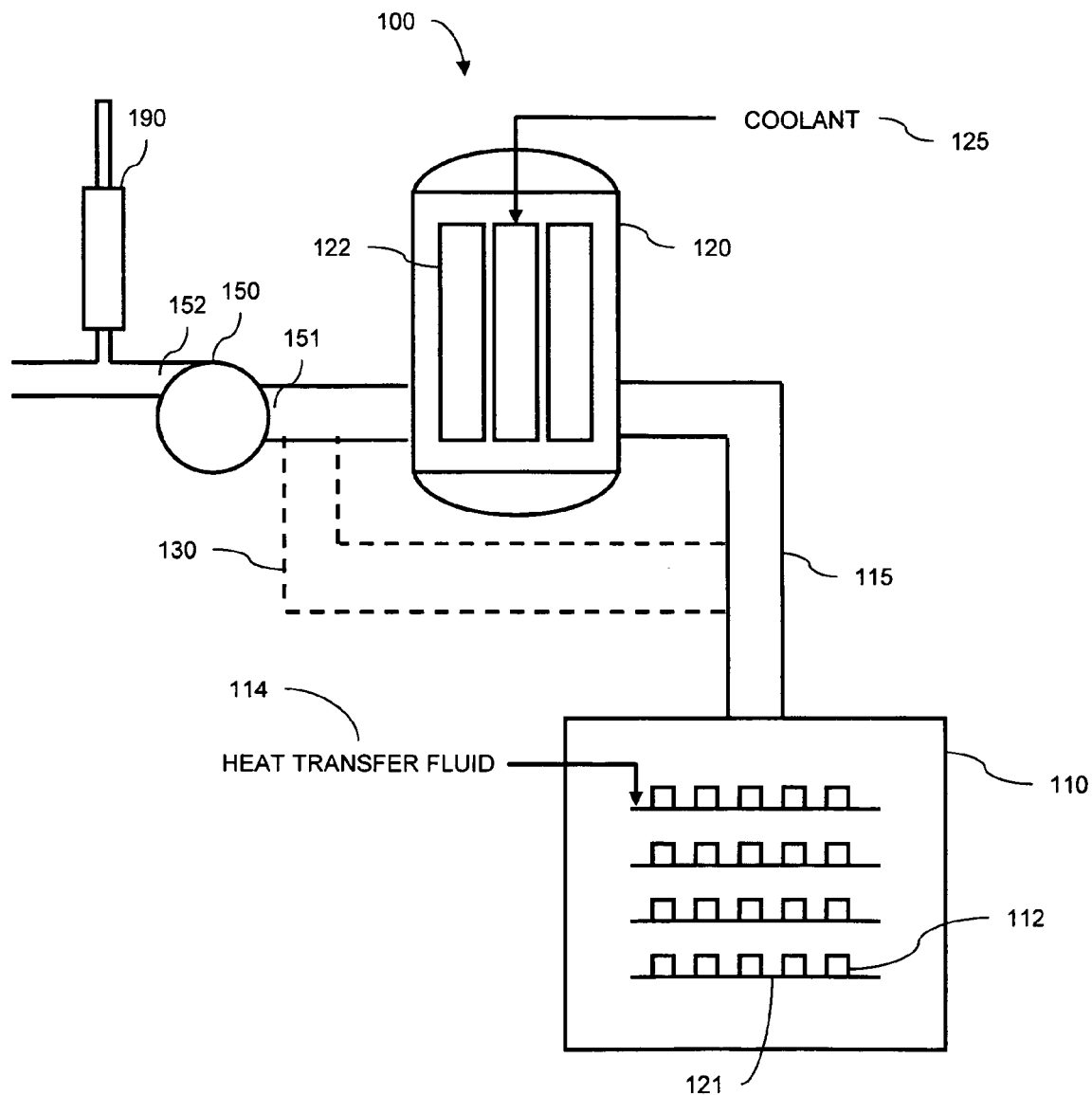
FIG. 1 is a schematic drawing of a freeze drying system according to one embodiment of the disclosure.

The present disclosure describes systems and methods for performing an emissions analysis on a specially conditioned gas stream. More specifically, the systems and methods of the present disclosure monitor a freeze drying process for malfunctions, and audit certain parameters of the process. To monitor conditions within the evacuated process chambers, compressed gases at the exhaust side of the vacuum pump are analyzed using gas analysis equipment 190 (FIG. 1) to determine the presence and concentration of trace amounts of certain non-condensable gases. That information is used to detect the presence and severity of leaks, and to measure process parameters.

Modern trace gas analysis equipment is capable of detecting concentrations even at the parts-per-billion (ppb) level. The resolution of those systems allows excellent discrimination between background gases and the gases to be determined. This disclosure presents a technique whereby such trace gas analysis equipment is placed on the high-pressure side of a vacuum pump in a freeze drying process. That technique makes possible several diagnostic tools for monitoring a freeze drying process, including the detection of small leaks of refrigerant and heat transfer fluids, the detection of vacuum leaks from atmosphere, the detection of residual cleaning materials, and the measurement of water vapor level during a secondary drying process. The discriminatory characteristics of the gas analysis equipment are critical for placing the equipment on the exhaust side of the vacuum pump, where oil from the pump, as well as other impurities, may otherwise overwhelm the trace gases to be detected.

Figure 2:
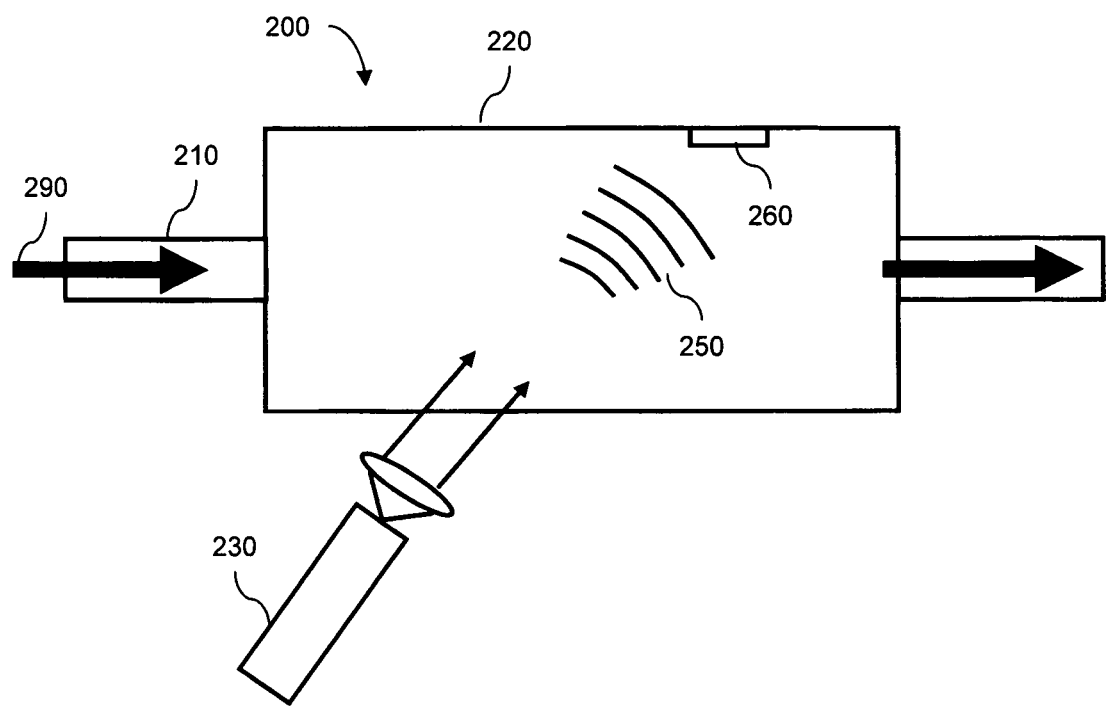
FIG. 2 is a schematic drawing of a prior art acousto-optic detection system.

One example of such trace gas analysis equipment is the acousto-optic spectrometer 200, shown schematically in FIG. 2. Acousto-optic spectrometry is a technology used in determining extremely low concentrations of gases. The technology is based on the generation of acoustic waves by the absorption of light energy. A gas mixture 290 from the vacuum pump high pressure outlet 152 (FIG. 1) and containing a target material is sampled through an inlet 210 into a chamber 220. In the chamber, an optical laser 230 in the mid-IR region is gated to impinge on the material in the chamber. When absorption takes place the gated absorption generates pressure waves 250 that can be picked up by an acoustic microphone 260. By tuning the laser to the correct absorption frequencies of the gas to be detected, the absorption level can be measured in a direct way. The sensitivity of acousto-optic spectrometry is at the ppb level. The measurements may be taken at atmospheric pressure or, in the case where a vacuum booster pump (not shown) is used downstream of the vacuum pump outlet, may be taken at subatmospheric pressure. Acousto-optic spectrometry is currently used in agricultural applications to measure ethylene that is a phytohormone interfering with ripening fruit.

Figure 3:
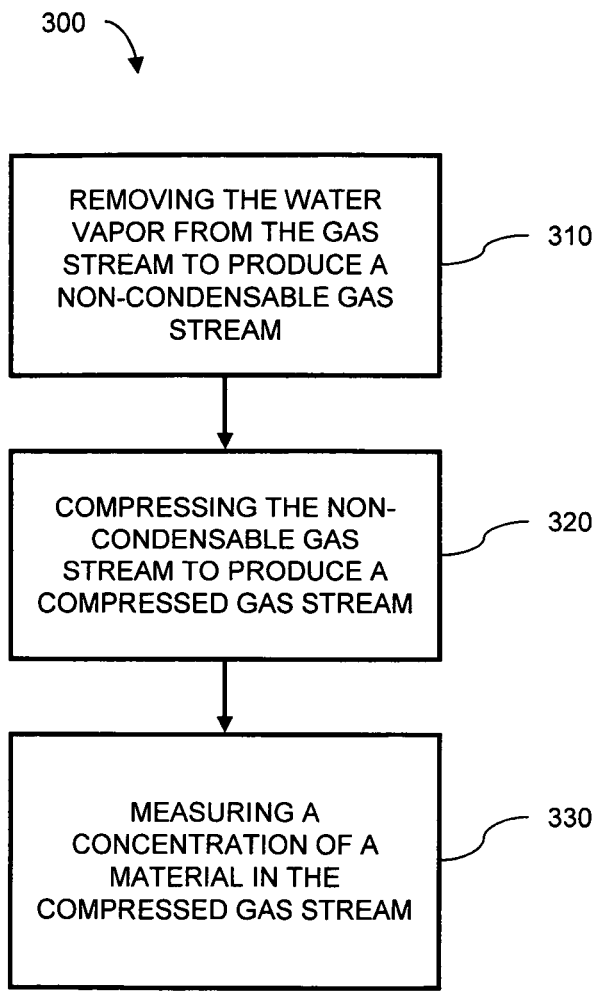
FIG. 3 is a flow chart showing a method in accordance with one aspect of the disclosure.

The inventors have discovered that gas analysis conducted on the high-pressure side of a vacuum pump may be used to monitor a freeze drying or similar process. The technique 300, shown in the flow chart of FIG. 3, is actually an emissions analysis of a specially conditioned gas stream for diagnostic purposes. The gas stream is conditioned by first removing water vapor from the gas stream at 310. In a freeze drying system, that step is performed by the condenser chamber, which condenses water from the gas stream as ice. The remaining non-condensable gas is compressed at 320. Compression in a freeze drying system is performed by a vacuum pump that compresses gases from the condensing chamber. The conditioned and compressed gas stream is then analyzed at 330 by a specific method.

Figure 4:
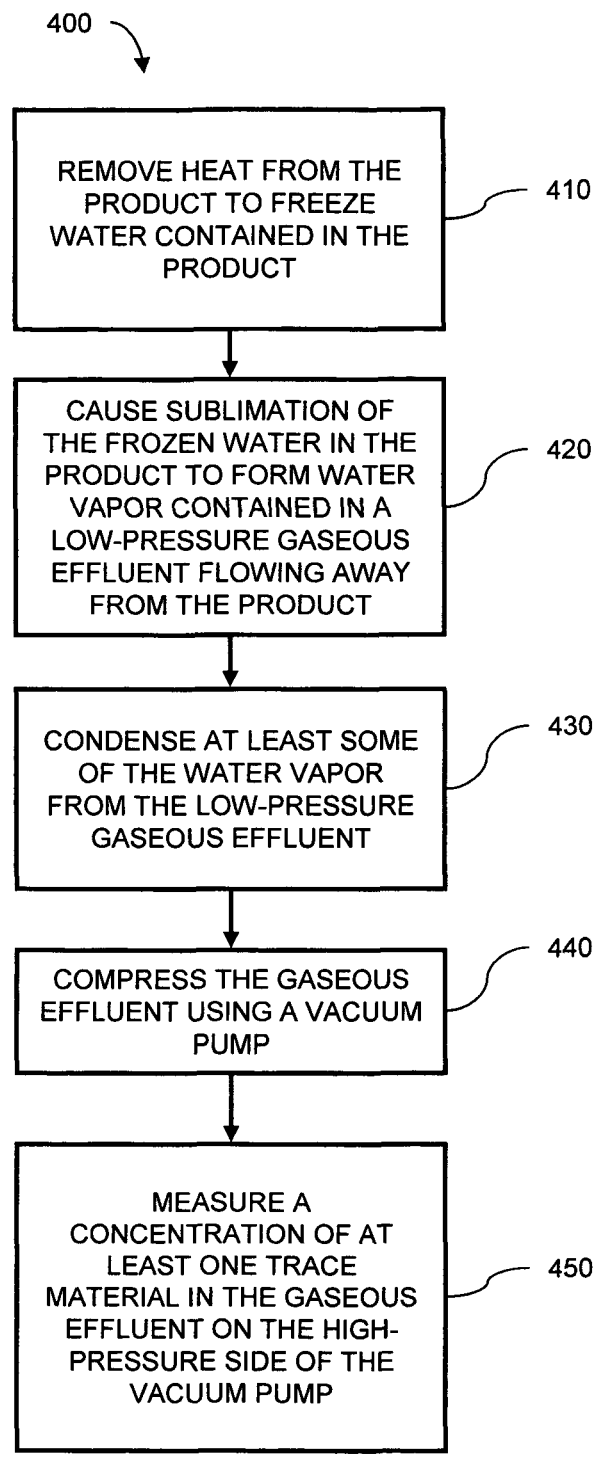
FIG. 4 is a flow chart showing a method in accordance with another aspect of the disclosure.

An exemplary embodiment 400 of the method, as applied to a freeze drying process, is illustrated by the flow chart of FIG. 4. Heat is removed from a product at 410 to freeze water contained in the product. The heat removal process is conducted in the freeze drying chamber, by forcing a heat transfer fluid through shelves that support the product. By subjecting the frozen product to vacuum conditions and a slight temperature increase, the frozen water in the product is sublimed at 420, forming water vapor. The water vapor is contained in a low pressure gaseous effluent that flows away from the product and out of the freeze drying chamber.

In a condensation chamber, the water vapor in the gaseous effluent is condensed at 430 as ice that accumulates on condensing surfaces. The condensing surfaces are cooled by a coolant that removes heat liberated by the condensation process. In one exemplary embodiment, the surfaces are cooled to temperatures of −70° C. to −90° C.

The non-condensable gases contained in the condensation chamber enter a low-pressure intake of a vacuum pump, where the non-condensable gases are compressed at 440. At the high-pressure exhaust of the vacuum pump, a concentration of trace materials in those compressed gases is measured at 450.

The analysis of gas exhaust from the vacuum pump may be conducted using acousto-optic spectrometry, as described above, or by any other technique capable of detecting trace amounts of material in an atmospheric gas. For example, multipass cavity-enhanced absorption spectrometry (CEAS) and cavity ring-down spectrometry (CRDS) may be used. In each case, the vacuum pump serves as a barrier between the measurement gauge and the sterile chambers, avoiding contamination of the chambers in keeping with the requirements of the pharmaceutical industry.

In one exemplary embodiment, the system monitors flow from the vacuum pump for the presence of heat transfer fluid that is contained within the shelves under normal circumstances. Presence of even trace amounts of that fluid in the vacuum pump exhaust may indicate leakage from the shelves into the freeze drying chamber.

The silicone oils used as heat transfer fluid in the shelves, as well as the refrigerant oils used in the condenser coils, have very distinct spectra which differ from the spectra of oils used in the common vacuum pumps. Where a spectrographic technique such as acousto-optic spectrometry, multipass cavity-enhanced absorption spectrometry (CEAS) or cavity ring-down spectrometry (CRDS) is used at the vacuum pump exhaust, a calibration on the height of the most important absorption peaks of the silicone heat transfer oils and/or refrigerant oils permits discrimination of those oils from each other, from oils used in the vacuum pump, and from any other materials that may be present in the vacuum pump exhaust.

The heat transfer oil may be a perfluorinated fluid that is easily detected via a halogen leak detector. One such halogen leak detector suitable for use in the presently described system is the D-TEK™ Select Refrigerant Leak Detector sold by Inficon of Syracuse, N.Y., USA. That device detects the absorption of infrared energy by a sample. The halogen leak detector is placed at the vacuum pump exhaust, as described above. The perfluorinated fluid is used either entirely as the heat transfer fluid, or is mixed with silicone oils in a quantity sufficient to be detected by the halogen leak detector.

The presently described system may also be used to detect coolant leakage from the condensation surfaces and coils in the condensation chamber. The coolant may be detectable using a halogen leak detector, as described above, or may be a material having distinct spectra that are monitored by other gas analysis equipment. As with the product shelf heat transfer fluid, the condenser coolant may be perfluorinated to facilitate detection in the vacuum pump exhaust.

A vacuum leak anywhere in the system may result in non-condensable contaminants in the vacuum pump exhaust. While difficult to detect in low concentration in the freeze drying and condensation chambers, those contaminants are compressed and concentrated by the vacuum pump and may be detected using the techniques of the present disclosure. For example, the gas analysis equipment may be configured to detect spectra of common organic and inorganic contaminants that may be in the ambient atmosphere. Those contaminants may occur naturally or may be introduced in the ambient atmosphere for purposes of detection by the system. Alternatively, the gas analysis equipment may be configured to detect any peak in the resulting spectrum that is not present during ordinary operation of the equipment. In that case, a signature or baseline spectrum may be established during a known problem-free run of the equipment. A later measured spectrum containing new peaks would be considered suspect.

Yet another application of the presently described system is the detection of trace gases remaining from materials that are used for other functions in the freeze dryer. For example, vaporized hydrogen peroxide ($H_2O_2$) or chlorine dioxide ($ClO_2$) is used as a sanitizing agent in freeze drying systems between cycles. Like the silicone oils discussed above, $H_2O_2$ has a very distinct spectrum in the mid-IR range. Measurements made by the gas analysis equipment may therefore be used to determine if the concentration of $H_2O_2$ is low enough to be acceptable for the initiation of production after a sterilization cycle.

With the advent of a new, more efficient generation of dry vacuum pumps, it may be possible to remove some amount of water from a product directly through the vacuum pump, without the use of a condensation chamber. For example, a secondary drying operation may be performed after most water is removed from the product using the condensation chamber. In one example, a bypass conduit 130 (FIG. 1) is used to bypass the condensation chamber 120, instead conducting gasses directly from the drying chamber 110 to the vacuum pump 150. The small amount of remaining moisture in the product 112 is sublimed and conducted directly through the vacuum pump 150. During that step, the condensation chamber 120 may be regenerated (i.e., ice removed) for the next cycle of primary drying.

During secondary drying, the rate of water vapor transport is very low. Currently-used measurement techniques placed in the vacuum portion of the freeze drying apparatus, such as tunable diode laser absorption spectroscopy (TDLAS), are complicated by the low concentrations. By placing the gas analysis equipment on the exhaust side of the dry vacuum pump, the concentration of water vapor can be deduced and that information may serve as an indicator of the average remaining moisture level in the product vials.

The above-described system, wherein the gas analysis is done on the atmospheric pressure side of the vacuum pump, has many advantages over currently-used systems. The reduced pressure gases are compressed on the exhaust side of the pump to atmospheric pressure. While concentrations of those gases may still be low at atmospheric pressure, there are more molecules that contribute to a specific signal leading to detectable levels, permitting a wider choice of chemical analysis techniques. In particular, optical spectroscopy technologies may be used.

Furthermore, where the analysis is done while the freeze drying process is in progress, such as in shelf leak detection, the exhaust gas to be analyzed has been stripped from the abundance of water vapor that would otherwise have swamped the signal. The water vapor is frozen out on condenser coils at low pressure before the gas stream reaches the vacuum pump. The vacuum pump compresses only the non-condensable gases, which reveal the condition of the freeze dryer during the drying process.

Because the gas analysis equipment is located outside the sterile zone of a freeze drying system, current freeze dryer applications may be retrofitted with the presently described system without the need for revalidation of the freeze drying process. Installations for use in industries such as the pharmaceutical industry are therefore faster and less costly.

The foregoing Detailed Description is to be understood as being in every respect illustrative and exemplary, but not restrictive, and the scope of the invention disclosed herein is not to be determined from the Description of the Invention, but rather from the Claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention.

What is claimed is:

1. A method for analyzing an exhaust gas stream from a freeze drying chamber which contains a solvent vapor, comprising the steps of:

removing the solvent vapor from the gas stream to produce a non-condensable gas stream;
compressing the non-condensable gas stream to produce a compressed gas stream; and
measuring, in the compressed gas stream, a concentration of a material.

2. The method of claim 1, wherein the freeze drying chamber includes hollow freeze drying shelves containing a heat transfer fluid, and the material measured in the compressed gas stream is heat transfer fluid leaking from the shelves.

3. The method of claim 2, wherein the heat transfer fluid contains a perfluorinated fluid, and the step of measuring a concentration of a material comprises measuring a concentration of the perfluorinated fluid using a halogen leak detector.

4. The method of claim 1, wherein the step of removing the solvent vapor from the gas stream comprises passing the gas stream through a condensation chamber containing cooled condensing surfaces.

5. The method of claim 4, wherein the measured material is a medium for cooling the condensing surfaces that is leaking into the condensation chamber.

6. The method of claim 1, further comprising the step of:
cleaning a process chamber used in the method with a cleaning material, and
wherein the measured material is residual cleaning material.

7. The method of claim 6, wherein the measured material comprises a material selected from the group consisting of hydrogen peroxide (H2O2) and chlorine dioxide (ClO2).

8. The method of claim 1, wherein the step of measuring a concentration of a material in the compressed gas stream further comprises using acousto-optic spectrometry to measure the concentration of the material.

9. The method of claim 1, wherein the step of measuring a concentration of a material in the compressed gas stream further comprises using a measurement technique selected from the group consisting of multipass cavity-enhanced absorption spectrometry (CEAS) and cavity ring-down spectroscopy (CRDS).

10. A method for freeze drying a product, the method comprising the steps of:

removing heat from the product to freeze a solvent contained in the product;
causing sublimation of the frozen solvent in the product to form a solvent vapor contained in a low-pressure gaseous effluent flowing away from the product;
condensing at least some of the solvent vapor from the low-pressure gaseous effluent to produce a non-condensable gas stream;
compressing the non-condensable gas stream using a vacuum pump to produce a compressed non-condensable gas stream; and
measuring, in the compressed non-condensable gas stream on a high-pressure side of the vacuum pump, a concentration of at least one trace material.

11. The method of claim 10, wherein the heat is removed from the product using hollow freeze drying shelves containing a heat transfer fluid.

12. The method of claim 11, wherein the material measured in the gaseous effluent is heat transfer fluid leaking from the shelves.

13. The method of claim 12, wherein the heat transfer fluid contains a perfluorinated fluid, and the step of measuring a concentration of at least one trace material comprises measuring a concentration of the perfluorinated fluid using a halogen leak detector.

14. The method of claim 10, wherein the step of condensing at least some of the solvent vapor from the low-pressure gaseous effluent comprises passing the low-pressure gaseous effluent through a condensation chamber containing cooled condensing surfaces.

15. The method of claim 14, wherein the material measured in the gaseous effluent is a medium for cooling the condensing surfaces.

16. The method of claim 10, further comprising the step of:
cleaning a process chamber used in the method with a cleaning material, and
wherein the material measured in the gaseous effluent is residual cleaning material.

17. The method of claim 16, wherein the material measured in the gaseous effluent comprises a material selected from the group consisting of hydrogen peroxide (H2O2) and chlorine dioxide (ClO2).

18. The method of claim 10, wherein the step of measuring a concentration of at least one trace material in the gaseous effluent on a high-pressure side of the vacuum pump further comprises using acousto-optic spectrometry to measure the concentration of the material.

19. The method of claim 10, wherein the step of measuring a concentration of at least one trace material in the gaseous effluent on the high-pressure side of the vacuum pump further comprises using a measurement technique selected from the group consisting of multipass cavity-enhanced absorption spectroscopy (CEAS) and cavity ring-down spectroscopy (CRDS).

20. A freeze dryer system, comprising:
a freeze drying chamber for containing product during a freeze drying process;
a condensation chamber in communication with the freeze drying chamber and comprising surfaces for condensing a solvent vapor from exhaust gas received from the freezer drying chamber;
a vacuum pump having a low pressure inlet and a high pressure outlet, the low pressure inlet of the vacuum pump being in communication with the condensation chamber, the vacuum pump being for producing a compressed exhaust gas; and
a testing apparatus connected for receiving the compressed exhaust gas from the high pressure outlet of the vacuum pump, the testing apparatus being for measuring, in the compressed exhaust gas, a presence of a material.

21. The system of claim 20, wherein the freeze drying chamber comprises hollow freeze drying shelves containing a heat transfer fluid.

22. The system of claim 21, wherein the testing apparatus measures trace amounts of heat transfer fluid from the shelves.

23. The system of claim 22, wherein the heat transfer fluid contains a perfluorinated fluid, and the testing apparatus is a halogen leak detector.

24. The system of claim 20, wherein the surfaces for condensing solvent vapor in the condensation chamber comprise cooled condensing surfaces.

25. The system of claim 24, wherein the testing apparatus measures trace amounts of a medium for cooling the condensing surfaces that is leaking into the condensation chamber.

26. The system of claim 20, wherein the testing apparatus measures trace amounts of a residual cleaning material used to clean the process chamber.

27. The system of claim 26, wherein the cleaning material comprises a material selected from the group consisting of hydrogen peroxide (H2O2) and chlorine dioxide (ClO2).

28. The system of claim 20, wherein the testing apparatus is an acousto-optic spectrometer.

29. The system of claim 20, wherein the testing apparatus is an apparatus selected from the group consisting of a multipass cavity-enhanced absorption spectrometer (CEAS) and cavity ring-down spectrometer (CRDS).

30. A method for freeze drying a product, the method comprising the steps of:
removing heat from the product in a freeze drying chamber to freeze a solvent contained in the product;
causing sublimation of the frozen solvent in the product to form a solvent vapor contained in a low-pressure gaseous effluent flowing away from the product;
compressing the gaseous effluent using a vacuum pump;
monitoring the freeze drying by measuring a concentration of the solvent vapor in the gaseous effluent on the high-pressure side of the vacuum pump.

\* \* \* \* \*